United States Patent
Charambura et al.

(10) Patent No.: US 6,610,311 B2
(45) Date of Patent: Aug. 26, 2003

(54) PACKAGED COSMETIC EFFERVESCENT CLEANSING PILLOW

(75) Inventors: Natalie Charambura, Fairfield, CT (US); Paul Roland Bergquist, Southport, CT (US); Craig Stephen Slavtcheff, Guilford, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/855,108

(22) Filed: May 14, 2001

(65) Prior Publication Data

US 2002/0037255 A1 Mar. 28, 2002

Related U.S. Application Data

(60) Provisional application No. 60/224,684, filed on Aug. 11, 2000.

(51) Int. Cl.⁷ ............................ A61K 9/00; A61K 9/46
(52) U.S. Cl. ................ 424/400; 434/464; 434/466; 434/43; 434/78.02
(58) Field of Search ................. 424/400, 404, 424/464, 466, 484, 43, 44, 47, 78.02

(56) References Cited

U.S. PATENT DOCUMENTS

| 4,118,890 A | * | 10/1978 | Shore | 47/29.3 |
| 4,762,230 A | * | 8/1988 | Croce | 206/469 |
| 4,853,211 A | * | 8/1989 | Kurobe et al. | 424/433 |
| 6,063,390 A | * | 5/2000 | Farrell et al. | 424/401 |

* cited by examiner

Primary Examiner—Thurman K. Page
Assistant Examiner—Robert M. Joynes
(74) Attorney, Agent, or Firm—Milton L. Honig

(57) ABSTRACT

A packaged effervescent product is provided which includes a sachet surrounded by an outer package film sealing the sachet against water vapor transmission. The sachet is a cosmetic article which includes an effervescent cleansing composition of an acid material such as citric add and an alkaline material such as sodium bicarbonate. The composition is held within the sealed sachet or pouch. At least one wall of the pouch is water permeable. The outer package film is formed of a material which must have a breathability for carbon dioxide. Any carbon dioxide generated during storage is thereby allowed to slowly diffuse into the atmosphere while still minimizing the amount of water which may enter the package.

11 Claims, No Drawings

PACKAGED COSMETIC EFFERVESCENT CLEANSING PILLOW

This application claims the benefit of Provisional Application No. 60/224,684, filed Aug. 11, 2000.

BACKGROUND OF THE INVENTION

1. Field of the Invention

The invention concerns a packaged cosmetic effervescent cleansing product.

2. The Related Art

Cosmetic products are continuously being sought which differentiate themselves from competitors in some manner. Breakthroughs can arise through a difference in product form. A product form departure has been described in U.S. Pat. No. 6,063,390 (Farrell et al.). A wiping article is therein described which includes an effervescent cleanser composition held within a pouch formed from a pair of substrate sheets. At least one of those substrate sheets is required to be water permeable. The effervescent composition is a mixture of an add material such as citric add and alkaline material such as sodium bicarbonate. Water contact causes the combination to effervesce. Skin benefit agents and a dry surfactant may be formulated within the composition.

Maintenance of product stability is a major challenge with this product form.

U.S. Pat. No. 6,063,390 suggests that the wiping article or pillow be packaged within a moisture impermeable outer package such as a laminated foil bag to prevent activation of the effervescent system during storage.

While working with the disclosed system, the present applicants found that outer packaging for moisture penetration prevention aggravated another problem. Adventitious moisture within the formulation, rather than merely seepage from the environment, caused a certain level of effervescence to occur. Carbon dioxide gases were thus generated. The outer packaging intended as a moisture barrier now represented a hindrance to elimination of built up carbon dioxide gases.

It is an object of the present invention to provide an outer package for a pouch containing an effervescent composition wherein the package not only will prevent moisture from penetrating to the composition but allows for release of any carbon dioxide gases which may be generated during storage.

Other objects of the present invention would become more readily apparent from consideration of the following summary and detailed description.

It is to be noted that the subsequently described invention is broader than the objects or technical problems it is directed to solve.

SUMMARY OF THE INVENTION

A package cosmetic article is provided for cleansing body surfaces, the article including:
  a pouch formed of walls, with at least one of the walls being water permeable, the pouch being sealed along all its perimeter; and
  an effervescent cleanser composition in the form of an anhydrous dry solid being positioned within the pouch, the composition including:
    (i) from about 1 to about 80% of an alkali material; and
    (ii) from about 0.5 to about 80% of an acid material;
wherein the pouch is sealed within an outer package formed of a film having breathability for carbon dioxide.

DETAILED DESCRIPTION OF THE INVENTION

It has been discovered through the present invention that outer packaging for cosmetic effervescent articles based on reaction of alkaline and acid materials must not only be a barrier protection from water vapor but also must be a breathable material allowing escape of any generated gases, especially carbon dioxide. Thus, the invention provides a sealed outer packaging material formed of a film having breathability. For purposes of this invention, breathability can be measured by ASTM D3985 intended to measure oxygen permeability but also useful for correlation to carbon dioxide permeability. When operated at 23° C./0% Relative Humidity, carbon dioxide gas permeability should range from about 100 to about 3,000, preferably from about 150 to about 2,000, more preferably from about 200 to about 1500 cc per 100 square inches per 24 hours. Among preferred materials for the outer sealing package film are polypropylene, polyethylene, polyvinyl chloride and polycarbonate. Polypropylene is most preferred. The materials may be employed as a single layer or as a series of laminated layers. Some of the layers may be formed of a material other than the preferred types, but with proviso that the composite film meets the requirement for carbon dioxide breathability. Film thicknesses may range anywhere from about 0.1 to about 5 mil, preferably from about 0.5 to about 3 mil, optimally from about 1 to about 2.5 mil.

Another feature of films suitable for the outer package material is that they have a Vapor Transmission Rate for water according to DIN 53122 (measured at 23° C./85% Relative Humidity) which ranges from about 0.001 to about 0.3, preferably from about 0.005 to about 0.1, more preferably from about 0.01 to about 0.1 grams per 100 square inches per 24 hours.

Most preferably, the film for the outer package material will be transparent. The sachet article will be viewable by a consumer through the transparent outer package. Aesthetics are therefore improved. Heat seals or adhesives may be employed along edges of the film to ensure a good seal.

Cosmetic wiping articles of the present invention when contacted with water billow to many times (more than 10 but often more than 40 times) their dry size when activated by water. The effervescent cleansing system exudes copious amounts of lather. A plumped "pillow" arises from the effervescent action. By careful control of the acidic and alkaline components, a squeaky clean rinsed feeling is felt on a user's skin.

A component of compositions for generating effervescence within the pouch is that of an acidic material. Suitable for this purpose are any adds present in dry solid form. Especially appropriate are $C_2$–$C_{20}$ organic mono- and polycarboxylic adds and especially alpha- and beta-hydroxycarboxylic acids; $C_2$–$C_{20}$ organophosphorus acids such as phytic acid; $C_2$–$C_{20}$ organosulfur acids such as toluene sulfonic add; and peroxides such as hydrogen peroxide. Typical hydroxycarboxylic acids include adipic, glutaric, succinic, tartaric, malic, maleic, lactic, salicylic and citric acids as well as acid forming lactones such as gluconolactone and glucarolactone. Most preferred is citric acid. Also suitable as acid material may be encapsulated acids. Typical encapsulating material may include water soluble synthetic or natural polymers such as polyacrylates (e.g. encapsulating polyacrylic acid), cellulosic gums, polyurethane and polyoxyalkylene polymers. By the term "acid" is meant any substance which when dissolved in deionized water at 1% concentration will have a pH of less than 7, preferably less than 6.5, optimally less than 5. These adds preferably at 25° C. are in solid form, i.e. having melting points no less than 25° C. Concentrations of the add should range from about 0.5 to about 80%, preferably from about 10 to about 65%, optimally from about 20 to about 45% by weight of the total composition.

Another component for generating the effervescent compositions of this invention within the pouch is that of an alkaline material. The alkaline material is a substance which can generate a gas such as carbon dioxide, nitrogen or oxygen, i.e. effervesce, when contacted with water and the acidic material. Suitable alkaline materials are anhydrous salts of carbonates and bicarbonates, alkaline peroxides (e.g. sodium perborate and sodium percarbonate) and azides (e.g. sodium azide). Preferably the alkaline material is sodium or potassium bicarbonate. Amounts of the alkaline material may range from about 1 to about 80%, preferably from about 5 to about 49%, more preferably from about 15 to about 40%, optimally from about 25 to about 35% by weight of the total composition.

By the term "anhydrous" is meant the presence of no more than 10%, preferably no more than 3.5% and optimally no more than 1% water by weight of the total composition. Water of hydration is not considered to be water for purposes of the anhydrous definition. However, it is preferred to minimize, preferably to eliminate any water of hydration.

Advantageously the combined amount of acidic and alkaline materials will be at least about 1.5%, preferably from about 40 to about 95%, optimally from about 60 to about 80% by weight of the total composition.

An optional but useful component of the compositions according to the present invention may be that of a dry surfactant, preferably a dry surfactant solid at 20° C. Most suitable for the present invention is sodium cocoyl isethionate. Other useful surfactants include sodium methyl cocoyl taurate and sodium lauryl sulfate. Surfactants may be of the anionic, cationic, nonionic, amphoteric, zwitterionic varieties and combinations thereof. Amounts of the dry surfactant may range from about 0.1 to about 30%, preferably from about 1 to about 30%, optimally from about 8 to about 15% by weight of the total composition.

A variety of skin benefit agents may be included to improve afterfeel properties. Advantageously these substances will be available as anhydrous dry powders. Alternatively these substances may be liquids deposited upon or into a powdered substrate (e.g. sodium bicarbonate or zeolite) to achieve a resultant dry flowing powder. Within the skin benefit agent scope are several categories of materials. These include emollients, antiaging actives, antibacterials and fungicides, skin lighteners, sunscreens and combinations thereof. Amounts of the skin benefit agents may range from about 0.001 to about 30%, preferably from about 0.1 to about 20%, more preferably from about 0.5 to about 10%, optimally between about 1 and about 5% by weight of the total composition.

Emollients may be in the form of natural or synthetic esters, silicone oils, hydrocarbons, starches, fatty acids and mixtures thereof. Typically the emollient may range in concentration from about 0.1 to about 35% by weight of the total composition.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid ester, diethylene glycol mono- and di-fatty acid esters, polyethylene glycol (200-6000) mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterols esters, of which cholesterol fatty add esters are examples thereof.
(6) Triglycerides such as sunflower seed oil, maleated sunflower seed oil, borage seed oil and safflower oil.

Hydrocarbons suitable as emollients include petrolatum, mineral oil, isoparaffins and hydrocarbon waxes such as polyethylene.

Starches are also suitable emollients. Typical of this class is tapioca and arabinogalactan.

Fatty acids may also be suitable as emollients. The fatty acids normally have from 10 to 30 carbon atoms. Illustrative of this category are pelargonic, lauric, myristic, palmitic, stearic, isostearic, hydroxystearic, oleic, linoleic, ricinoleic, arachidic, behenic and erudc acids.

Antiaging actives are also useful as skin benefit agents. Included within this category are vitamins, retinoids and combinations thereof. Amounts of these materials may range from about 0.001 to about 20% by weight of the total composition. Suitable vitamins include ascorbic acid, Vitamin $B_6$, Vitamin $B_{12}$, tocopherol as well as salts and $C_1$–$C_{20}$ esters thereof. Suitable retinoids include retinoic acid as well as its $C_1$–$C_{22}$ esters and salts, retinol and $C_1$–$C_{22}$ fatty esters of retinol including retinyl linoleate.

Another class of antiaging actives are the alpha- and beta-hydroxycarboxylic acids and salts thereof. Representative of this group are glycolic acid, lactic add, malic add, hydroxyoctanoic add and mixtures of these as well as their salts. Suitable salts are the alkalimetal, ammonium and $C_1$–$C_{10}$ alkanol ammonium salts.

Antibacterials and fungicidals may also be included as skin benefit agents. Representative of these categories are triclosan, triclocarban, hexetidene, gluconates, zinc salts (e.g. zinc citrate and zinc phenolsulfonate) and combinations thereof.

Skin lighteners may also be included under the skin benefit agents. Typical of this category are niacinamide, kojic acid, arbutin, vanillin, ferulic acid and esters thereof, resorcinol, hydroquinone, placental extract and combinations thereof.

Sunscreens may also be included as skin benefit agents. Particularly preferred are such materials as ethylhexyl p-methoxycinnamate, available as Parsol® MCX, and benzophenone-3, also known as Oxybenzone. Inorganic sunscreen actives may be employed such as microfine titanium dioxide, polyethylene and various other polymers. Amounts of the sunscreen agents will generally range from 0.1 to 30%, preferably from 2 to 20%, optimally from 4 to 10% by weight.

Adjunct functional agents may also be incorporated into compositions of the present invention. These include electrolytes, thickeners and mixtures thereof. Amounts of these substances may range from about 0.1 to about 20%, preferably from about 0.3 to about 10%, optimally between about 0.5 and about 5% by weight of the total composition.

Electrolytes may be selected from alkali, alkaline earth or ammonium salts of phosphates, silicates, halides, sulphates and mixtures thereof. Typical phosphates are potassium polymetaphosphate, sodium tripolyphosphate, sodium tetrapyrophosphate, sodium or potassium pyrophosphate and sodium hexametaphosphate. Most preferred is potassium polymetaphosphate available as Lipothix 100B® which is a 70:30 mixture of potassium polymetaphosphate and sodium bicarbonate, available from Lipo Chemicals, Inc., Paterson, N.J. Preferred sulphates are the magnesium sulphates.

Thickeners which may improve afterfeel properties on skin include inorganic or organic substances. A particularly preferred inorganic thickener is sodium magnesium silicate commercially available as Optigel SH®. Organic thickeners include alginic acid as well as sodium and calcium alginates, sodium carboxymethyl cellulose, hydroxypropyl methylcellulose, hydroxypropyl cellulose, hydroxyethyl cellulose and combinations thereof. Most preferred is alginic acid commercially available as Kelacid® from Sud-Chemie Rheologicals, Louisville, Ky. Alginic acid is highly effective at removing the slimy feel associated with deposits of alkaline material which are not fully rinsed away from the skin. Amounts of the thickener may range from about 0.1 to about 20%.

Polysaccharides useful in this invention are dry solid anhydrous substances such as sorbitol, sugars, (such as trehalose) starches, modified starches (e.g. aluminum octenyl succinate) and mixtures thereof. Most preferred is sorbitol.

Deposition aids may also be incorporated in compositions of the present invention. These assist in depositing skin benefit agents onto the skin surface. Particularly effective are cationic monomers and polymers for this purpose.

Most preferred for purposes of this invention are Polymer JR and cationic guar gums such as Jaguar C13S® which is guar hydroxypropyltrimonium chloride. Amounts of the deposition aid may range from about 0.01 to about 1%, preferably from about 0.05 to about 0.5%, optimally from about 0.1 to about 0.3% by weight.

Advantageously an emotive agent such as a fragrance and/or botanical extract are included with the effervescent cleansing composition. Fragrances and botanicals are often liquids. For this reason it is necessary to uniformly distribute and allow absorption of liquid components into the solid powder. One method of best achieving this is to spray these liquids onto the solids. Amounts of the fragrance and/or botanicals combined may be at levels from abut 0.1 to about 3%, preferably from 0.5 to 2%, optimally from 0.8 to 1.5% by weight of the total composition.

The term "fragrance" is defined as a mixture of odoriferous components, optionally mixed with a suitable solvent diluent or carrier, which is employed to impart a desired odor. Particular preferred odoriferous components are cyclic and acyclic terpenes and terpenoids. These materials are based upon isoprene repeating units.

Preservatives can desirably be incorporated into the cosmetic compositions of this invention to protect against the growth of potentially harmful microorganisms. Suitable traditional preservatives for compositions of this invention are alkyl esters of para-hydroxybenzoic acids. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the sue of the composition and possible incompatibilities between the preservatives and other ingredients in the emulsion. Preservatives are preferably employed in amounts ranging from 0.01% to 2% by weight of the composition.

Natural vegetable materials from renewable resources are often desirable in cosmetic compositions. For instance, cosmetic compositions of the present invention may include beta-glucan derived from oats, commercially available under the trademark Microat SF from Nurture Inc., Missoula, Mont.

Colorants may also be included in compositions of the present invention. These substances may range from about 0.05 to about 5%, preferably between 0.1 and 3% by weight.

Effervescent cleansing compositions of this invention will be placed within a pouch formed between a first and second flexible substrate sheet, preferably at least one of these being a flexible sheet At least one of the sheets must be water permeable, most preferably both sheets should have water permeability. For definitional purposes, first and second sheets can be folded-over panels of a single unitary sheet Suitable materials for forming sheets may be rayon, polyester, polyethylene, polypropylene, cotton or any combination thereof. These sheets may be woven or non-woven. Most preferred is a non-woven rayon. Cellulosic paper fiber substrates are best not employed because of their insufficient wet-strength although they may be blended with other fibers referenced above; it is important that the substrate sheets are not readily torn open through consumer rubbing of the article. Unlike laundry sachet articles, pouches of the present invention should not rupture to allow dispersion of their granular contents into wash water. Rather it is intended for all cleanser composition components to exit by dissolution through the permeable walls of the pouch.

Skin surfaces against which articles of the present invention are useful include face, body, scalp, axilla and even legs/feet. When the article is a foot cleanser, it would be advantageous for the pouch on one of its sides to be coarse while the second of the sheets may be soft and gentle. An abrasive non-woven flexible sheet in a foot cleanser product is useful for rubbing against calluses while the second sheet of the pouch remains smooth.

Articles according to the present invention may be formed in the following manner. Constituents of the effervescent cleansing composition are placed into a dry mill or similar apparatus and blended until a uniformly distributed powder results. Thereafter, fragrance/botanical component as a Phase B is sprayed into the dry mill with concurrent agitation of the powdered composition.

A continuous roll of first substrate sheet is unwound from a source roll over a moving conveyer belt. The effervescent cleansing composition is placed into a hopper positioned over the conveyer belt. A discrete charge of powdered composition is regularly placed on the first substrate sheet at a location directly under a nozzle of the hopper. A second substrate sheet is then in register placed over that of the loaded first substrate sheet. At this point all four corners defining a rectangle or square are sealed in register trapping the effervescent cleansing composition within. Cutters then separate one sealed section from another thereby forming the wiping article.

Ultrasonic welding may be employed as an alternative to heat-sealing of the first and second substrates together. Thread stitching, glue application or other closure mechanisms may also be utilized.

One or more of the wiping articles are then packaged, within an outer packaging film sheet which meets the water and carbon dioxide Vapor Transmission Rate hereinabove described. Particularly useful are polypropylene clear transparent films. A single sheet of such film is wrapped around the sachet wiping article and the edges of the film are heat sealed to enclose the sachet.

Except in the operating and comparative examples, or where otherwise explicitly indicated, all numbers in this description indicating amounts of material are to be understood as modified by the word "about".

The term comprising is meant not to be limiting to any subsequently stated elements but rather to encompass non-specified elements of major or minor functional importance. In other words the listed steps, elements or options need not be exhaustive.

The following examples will more fully illustrate embodiments of this invention. All parts, percentages and proportions referred to herein and in the appended claims are by weight unless otherwise indicated.

EXAMPLE 1

An effervescent cleansing composition was prepared according to the formulation reported in Table I. Phase A was dry blended in a high speed shearing mixer. Fragrance was then sprayed onto the resultant powder as a Phase B. Three grams of the resultant powder were then placed into a two inch by three inch pouch formed of non-woven rayon. All sides were closed by double stitching with thread.

TABLE I

| INGREDIENT | WEIGHT % |
| --- | --- |
| PHASE A | |
| Sodium Bicarbonate | 34.5 |
| Citric Acid (Anhydrous) | 40.4 |
| Sodium Cocoyl Isethionate (Powder) | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| PHASE B | |
| Fragrance | 1.0 |

The resultant pouches were then sealed within a 2.0 mil thick clear polypropylene wrapper. Heat was applied to both ends of the wrapper thereby sealing the pouch within the polypropylene film.

EXAMPLE 2

Another effervescent cleansing composition may be prepared according to the formulation reported in Table II.

TABLE II

| INGREDIENT | WEIGHT % |
| --- | --- |
| PHASE A | |
| Sodium Bicarbonate | 32.3 |
| Citric Acid (Anhydrous) | 41.1 |
| Sodium Cocyl Isethionate (Powder) | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| Laracare A200 ® (Arabinogalactan) | 1.0 |
| Ascorbic Acid | 0.5 |
| PHASE B | |
| Fragrance | 1.0 |

The resultant pouches are then sealed within a 1.8 mil thick clear polypropylene laminate wrapper. Heat is applied to both ends of the wrapper thereby sealing the pouch within the polypropylene film.

EXAMPLE 3

A face cleansing effervescent composition may be prepared according to the formulation reported in Table III.

TABLE III

| INGREDIENT | WEIGHT % |
| --- | --- |
| PHASE A | |
| Sodium Bicarbonate | 33.6 |
| Citric Acid (Anhydrous) | 39.0 |
| Sodium Isethionate Powder | 3.0 |
| Sodium Methyl Cocoyl Taurate | 6.0 |
| Sodium Lauryl Sulfate | 2.5 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 2.0 |
| Tapioca | 5.5 |
| Methyl Gluceth 20-Benzoate | 2.0 |
| Guar Hydroxypropyl Trimonium Chloride | 0.25 |
| PHASE B | |
| Fragrance | 0.65 |

The resultant pouches are then sealed within a 1.6 mil thick high-density polyethylene wrapper. Heat is applied to both ends of the wrapper thereby sealing the pouch within the polypropylene film.

EXAMPLE 4

A still further effervescent cleansing composition according to the-present invention may be prepared according to the formulation reported under Table IV. Phase A is prepared by dry mixing of the ingredients in a high speed shear mixer. Three grams of resultant powder are placed into a two inch by three inch pouch formed of non-woven cotton polyester (50:50). The mesh size of the pouch walls is sufficient to allow transfer of dissolved ingredients. All sides of the pouch are welded by ultrasonic heat to insure against powder escaping from the pouch.

TABLE IV

| INGREDIENT | WEIGHT % |
|---|---|
| PHASE A | |
| Potassium Bicarbonate | 29.5 |
| Lactic Acid (Anhydrous) | 45.4 |
| Sodium Sulfosuccinate | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| PHASE B | |
| Fragrance | 1.0 |
| Licorice Extract | 0.1 |

The resultant pouches are then sealed within a 1.2 mil thick opaque polycarbonate wrapper. Heat is applied to both ends of the wrapper thereby sealing the pouch within the polypropylene film.

EXAMPLE 5

Still another effervescent cleansing composition is prepared according to the formulation reported in Table V. The ingredients are dry blended in a high speed shearing mixer. Fragrance and herbal extract are sprayed onto the powder and further blended to achieve homogeneity. Three grams of the resultant powder are placed into a two inch by three inch pouch formed of non-woven polypropylene. All sides are closed by convection heat sealing along the perimeter thereof.

TABLE V

| INGREDIENT | WEIGHT % |
|---|---|
| PHASE A | |
| Sodium Bicarbonate | 29.5 |
| Citraconic Acid (Anhydrous) | 45.4 |
| Methyl Glucamide | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| PHASE B | |
| Fragrance | 0.9 |
| Yarrow | 0.1 |

The resultant pouches are then sealed within a 1.4 mil thick clear polypropylene wrapper. Heat is applied to both ends of the wrapper thereby sealing the pouch within the polypropylene film.

EXAMPLE 6

A series of plastic films were evaluated for breathability allowing escape of carbon dioxide. Carbon dioxide trans mission rates were evaluated utilizing ASTM D3985. Test conditions were as follows:

Side 1 of Barrier=760 mm Hg, 100% $CO_2$
Side 2 of Barrier=760 mm Hg, 100% $N_2$
Relative Humidity: Side 1 of Barrier=0% Side 2 of Barrier=0%

TABLE VI

| PLASTIC FILM | MEASURED TRANSMISSION RATE cc (100 in$^2$/24 hrs.) |
|---|---|
| Polypropylene A | 411 |
| Polypropylene B | 399 |
| Polyethylene A | 1398 |
| Polyethylene B | 1497 |
| Polyethylene Terephthalate (PET) A | 45.3 |
| Polyethylene Terephthalate (PET) B | 42.1 |
| Polyvinylchloride A | 1057 |
| Polyvinylchloride B | 1045 |

*Film thickness = 1 mil

Levels below about 100 cc per 100 in$^2$/24 hrs. insufficiently allow carbon dioxide gas to escape. PET with values no higher than 45.3 as measured and reported in Table VI is seen as an unsuitable barrier packaging. By contrast, polypropylene, polyethylene and PVC all exhibited sufficient breathability with values very substantially above the minimum 100.

Water vapor transmission through the film surrounding the effervescent cleanser containing pouch should be held to a minimum. Inhibition of water vapor transmission is excellent with polypropylene. Transmission is somewhat higher with PET and PVC.

The foregoing description and examples illustrate selected embodiments of the present invention. In light thereof variations and modifications will be suggested to one skilled in the art, all of which are within the spirit and purview of this invention.

What is claimed is:

1. A packaged cosmetic article for cleansing body surfaces, the article comprising:
    a pouch formed of walls, with at least one of the walls being water permeable, the pouch being sealed along all its perimeter; and
    an effervescent cleanser composition in the form of an anhydrous dry solid being positioned within the pouch, the composition comprising:
        (i) from about 1 to about 80% of an alkali material; and
        (ii) from about 0.5 to about 80% of an acid material;
    wherein the pouch is sealed within an outer package formed of a film having breathability for carbon dioxide.

2. The article according to claim 1 wherein the outer package film is selected from the group consisting of polypropylene, polyethylene, polyvinyl chloride and polycarbonate.

3. The article according to claim 1 wherein the outer package film comprises polypropylene.

4. The article according to claim 1 wherein the outer package film has a thickness ranging from about 0.1 to about 5 mil.

5. The article according to claim 1 wherein the outer package film has a thickness ranging from about 0.8 to about 1.8 mil.

6. The article according to claim 1 wherein the film is transparent.

7. The article according to claim 1 further comprising from about 0.01 to about 30% by weight of a skin benefit agent selected from the group consisting of emollients, anti-aging actives, antibacterials and fungicides, skin lighteners, sunscreens and mixtures thereof.

8. The article according to claim 6 wherein the anti-aging actives are selected form the group consisting essentially of vitamins, retinoids and mixtures thereof.

9. The article according to claim 1 further comprising from about 0.1 to about 3% by weight of an emotive agent selected from the group consisting of fragrance, botanical and mixtures thereof.

10. The article according to claim 1 wherein the acid is citric acid.

11. A packaged cosmetic article for cleansing body surfaces, the article comprising:

a pouch formed of walls, with at least one of the walls being water permeable, the pouch being sealed along all its perimeter; and an effervescent cleanser composition in the form of an anhydrous dry solid being positioned within the pouch, the composition comprising:

(i) from about 1 to about 80% of alkali material; and (ii) from about 0.5 to about 80% of an acid material;

wherein the pouch is sealed within an outer package formed of a film having carbon dioxide permeability ranging from about 100 to about 3,000 cc per 100 square inches per 24 hrs. measured at 23° C./0% Relative Humidity, and a Vapor Transmission Rate for water ranging from about 0.001 to about 0.3 grams per 100 square inches per 24 hrs. measured at 23° C./85% Relative Humidity.

* * * * *